United States Patent
Chen et al.

(10) Patent No.: US 7,048,844 B2
(45) Date of Patent: May 23, 2006

(54) GAS SENSOR AND METHOD FOR USE THEREOF

(75) Inventors: David K. Chen, Rochester Hills, MI (US); Da Yu Wang, Troy, MI (US); Yingjie Lin, El Paso, TX (US); Raymond L. Bloink, Swartz Creek, MI (US); Devesh Srivastava, Flint, MI (US); Walter T. Symons, Grand Blanc, MI (US); Kaius K. Polikarpus, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 485 days.

(21) Appl. No.: 10/295,338

(22) Filed: Nov. 15, 2002

(65) Prior Publication Data

US 2004/0094416 A1    May 20, 2004

(51) Int. Cl.
*G01N 27/407* (2006.01)

(52) U.S. Cl. .................... 205/789.5; 205/787; 204/426

(58) Field of Classification Search ............... 204/412, 204/421, 424–429, 431, 432; 205/783–786, 205/787
See application file for complete search history.

(56) References Cited

U.S. PATENT DOCUMENTS

| | | | | |
|---|---|---|---|---|
| 4,905,652 A | * | 3/1990 | Nakajima et al. ............ | 123/679 |
| 6,214,208 B1 | * | 4/2001 | Ando et al. .................. | 205/781 |
| 6,382,198 B1 | | 5/2002 | Smith et al. ................. | 123/673 |
| 6,447,658 B1 | | 9/2002 | Wu et al. .................... | 204/424 |
| 6,453,726 B1 | | 9/2002 | Gutierrez et al. .......... | 73/31.05 |
| 6,514,397 B1 | | 2/2003 | LaBarge et al. ............ | 204/424 |
| 6,544,467 B1 | | 4/2003 | Symons et al. ............. | 264/618 |
| 6,555,159 B1 | * | 4/2003 | Clyde et al. ............. | 427/126.3 |
| 6,562,747 B1 | | 5/2003 | Symons et al. ............. | 501/103 |
| 6,579,435 B1 | | 6/2003 | Wang et al. ................. | 204/425 |
| 6,579,436 B1 | | 6/2003 | Wang et al. ................. | 204/425 |
| 6,585,872 B1 | | 7/2003 | Donelon et al. ............ | 204/424 |
| 6,616,820 B1 | | 9/2003 | Wang et al. ................. | 204/411 |
| 6,638,405 B1 | | 10/2003 | Jain et al. ................... | 204/421 |
| 6,638,416 B1 | * | 10/2003 | Wang et al. ................. | 205/775 |

* cited by examiner

*Primary Examiner*—Kaj K. Olsen
(74) *Attorney, Agent, or Firm*—Jimmy L. Funke

(57) ABSTRACT

A sensor comprises: a pump cell comprising an inner pump electrode, an outer pump electrode, a pump cell electrolyte layer interposed between the inner pump electrode and the outer pump electrode and a cell isolation layer disposed on the inner pump electrode on a side opposite the pump cell electrolyte, wherein the outer electrode is in fluid communication with a reducing gas. A reference cell is in operable communication with the pump cell, the reference cell comprising an outer reference electrode and an inner reference electrode, and a reference cell electrolyte interposed between the outer reference electrode and the inner reference electrode. A diffusion limiting material flanks both sides of a chamber formed between the cell isolation layer and a cell separation layer, wherein the cell separation layer comprises a via coaxial and in fluid communication with the inner pump electrode, the diffusing limiting material, and the outer reference electrode, and wherein the diffusion limiting material has a gas permeability such that the limiting current of oxygen in air is about 0.05 mA to about 5 mA per cm² of pump electrode area.

15 Claims, 3 Drawing Sheets

GAS SENSOR AND METHOD FOR USE THEREOF

TECHNICAL FIELD

The present disclosure relates to a sensor. In particular, the present disclosure relates to a sensor capable of linearly signalling oxygen output at low temperature operating conditions, and to a method for such linear detection.

BACKGROUND OF THE INVENTION

The automotive industry has used various gas sensors in automotive vehicles for many years. For example, electrochemical sensors based on polarographic principles have been developed for determining the concentration of oxygen or unburned components in exhaust gases produced by an internal combustion engine or a motor vehicle. These types of oxygen sensors typically include a pump cell and a Nernst cell built, for example, from solid oxide electrolyte materials such as doped zirconia, and linked together through an external electrical circuit. The Nernst cell includes an air reference electrode (or a biased reference electrode) and a sensing electrode with a solid electrolyte therebetween. The pump cell includes a first and second electrode with a solid electrolyte therebetween and a gas chamber with an aperture. The first electrode of the pump cell and the sensing electrode of the Nernst cell are exposed to the gas chamber that receives a representative flow of test gas, such as engine exhaust gas. A controlled electrical potential is applied to the pump cell to pump oxygen into and out of the gas chamber to maintain the electromotive force of the Nernst cell as sensed at the air reference electrode thereof at a desired potential.

To provide for sensing of the oxygen concentration in the test gas, such as by sensing oxygen flux in the gas chamber, the sensor must be maintained in a current limiting range of operation by maintaining the Nernst potential applied to the sensor within a predetermined voltage range. The current limiting range of operation is characterized by a sensor output current that is insensitive to variations in the potential applied to the pump cell. In such a range of operation, the aperture limits gas flux into or out of the gas chamber and sensor output current indicates the maximum flow that can be supported by the concentration in the test gas. If the potential is above the predetermined Nernst voltage range, additional oxygen may be stripped from gas species such as water ($H_2O$) and carbon dioxide ($CO_2$), skewing the relationship between the gas concentration and sensor output current. If the potential is below the predetermined Nernst voltage range, an excess of oxygen is available and sensor output current does not indicate oxygen concentration but rather is a nonlinear function of the gas concentration.

Current sensors such as the oxygen sensors described above are inadequate for determining hydrogen concentration in an air environment. For example, when the sensor is operating in an air environment, it needs to operate at a very high temperature, typically above 700° C. to be able to pump all the oxygen.

There are also solid electrolytes that can conduct protons instead of oxygen ions. They can substitute the zirconia electrolyte of the above mentioned device in order to perform hydrogen or hydrocarbon (linear) sensing in air. However, these electrolytes are not chemically stable and will dis-integrate during sensing operation. Additionally, the chemically stable proton conducting electrolytes are not conductive enough to pump protons to the limiting value without getting into the electrolysis range. Thus, it is desirable to have a hydrogen sensing device that is stable, is operable at temperatures below about 600° C., and preferably that is sensitive to hydrogen or hydrocarbon concentrations, or to other gases such as CO, in air environment.

SUMMARY

Disclosed herein is a sensor comprising a pump cell comprising an inner pump electrode, an outer pump electrode, a pump cell electrolyte layer interposed between the inner pump electrode and the outer pump electrode and a cell isolation layer disposed on the inner pump electrode on a side opposite the pump cell electrolyte, wherein the outer electrode is in fluid communication with a reducing gas. A reference cell is in operable communication with the pump cell, the reference cell comprising an outer reference electrode and an inner reference electrode, and a reference cell electrolyte interposed between the outer reference electrode and the inner reference electrode. A diffusion limiting material flanks both sides of a chamber formed between the cell isolation layer and a cell separation layer, wherein the cell separation layer comprises a via coaxial and in fluid communication with the inner pump electrode, the diffusing limiting material, and the outer reference electrode, and wherein the diffusion limiting material has a gas permeability such that the limiting current of oxygen in air is about 0.05 mA to about 5 mA per $cm^2$ of pump electrode area.

Further disclosed is a method for measuring reducing gas concentrations in a gas comprising: exposing the sensor to air, applying a voltage to the outer pump electrode and the inner pump electrode to form a limiting current, diffusing oxygen molecules and reducing gases across the diffusion limiting material, generating an electromotive force signal between the outer reference electrode and the inner reference electrode, and adjusting the pump current to maintain the electromotive force signal at a predetermined value, wherein the limiting current is proportional to the reducing gases.

The above-described and other features will be appreciated and understood by those skilled in the art from the following detailed description, drawings, and appended claims.

BRIEF DESCRIPTION OF THE DRAWINGS

Referring now to the drawings, in which.

DESCRIPTION OF THE PREFERRED EMBODIMENT

Disclosed herein is a sensor operable by means of a pump cell mechanism. Furthermore, the sensor can operate at temperatures below the auto-ignition temperatures of gases contained within the sensor, and can produce linear oxygen output signals, which is also gives linear signal to reducing gas concentration.

Figure 1:
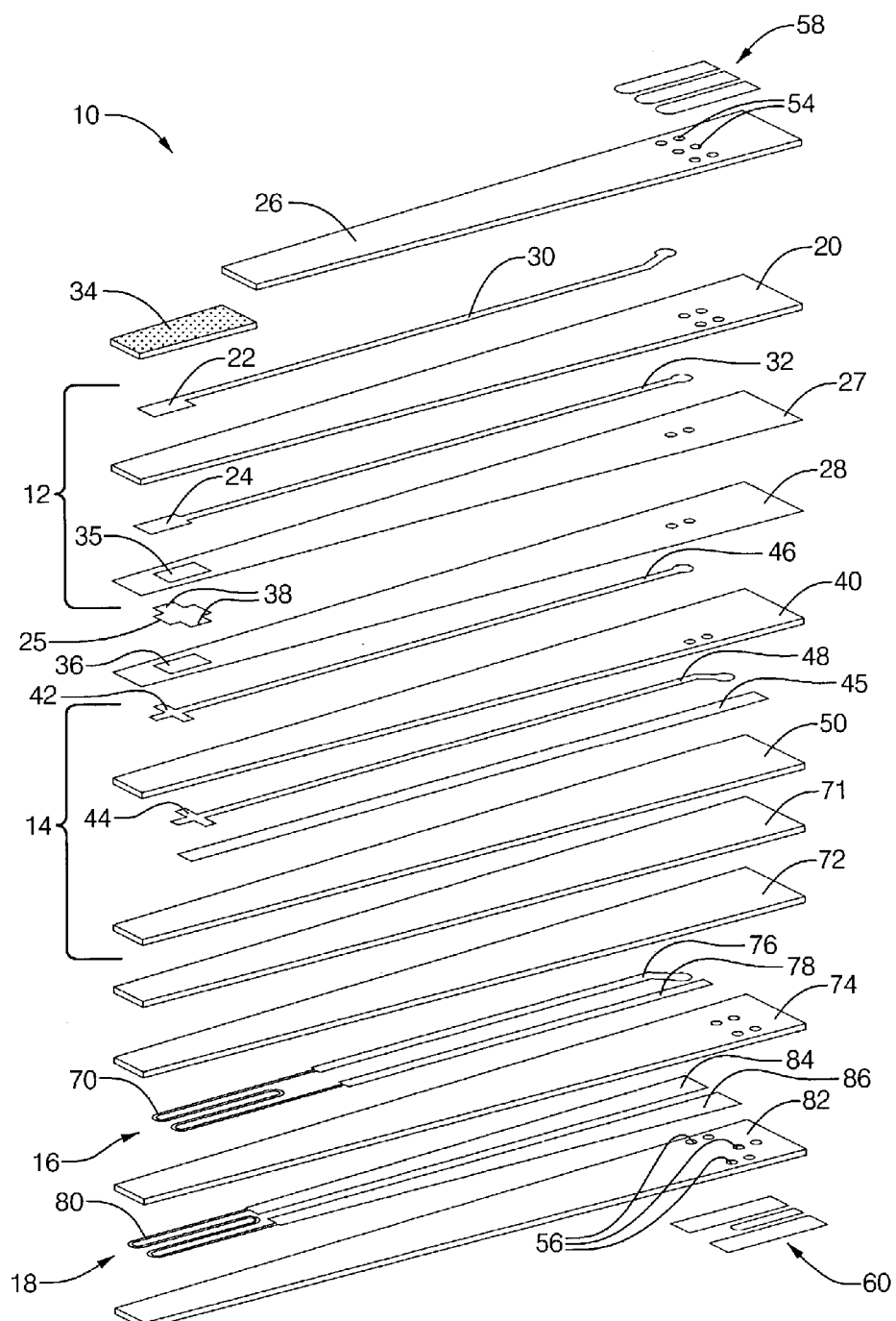
FIG. 1 is a schematic representation of a side-elevational view of the sensor.

An exemplary sensor is shown in FIG. 1, wherein the sensor is generally designated by reference numeral 10. The sensor 10 comprises two electrochemical cells: a pump cell 12 and a reference cell 14. The electrochemical cells are physically separated by a cell separation layer 28. Disposed on a surface of the cell separation layer 27 and separating layer 28 on the side opposite to the reference cell 14 is a chamber 25. The chamber 25 comprises a space wherein oxygen and other reference and/or ambient gases may collect and react with each other. Flanking the chamber 25 on both sides, and in physical communication with the chamber 25 is a diffusion limiting material 38. Preferably, the sensor 10 further includes other components, such as a temperature sensor 16, a heater 18, lead getting layer, ground plane, and/or the like.

The pump cell 12 comprises an ionically conductive pump cell electrolyte 20, an outer pump electrode 22 and an inner pump electrode 24 disposed on each major surface of the pump cell electrolyte 20 and preferably, an insulating layer 26 and cell isolation layer 27 disposed on sides of the outer and inner pump electrodes 22, 24 opposite the pump cell electrolyte 20. Conductive leads 30, 32 extend from each pump electrode 22, 24, respectively. Preferably disposed on the exterior side of the outer pump electrode 22 and adjacent to the insulating layer 26 is a porous protection layer 34, which protects the outer pump electrode 22 from impurities that can cause poisoning or degradation in electrode sensitivity. Alternatively, the porous protection layer 34 may be integrated into the insulating layer 26.

The sensor 10 may also comprise a reference cell 14, which is disposed on the cell separation layer 28 on the side opposite the diffusion limiting material 38. The reference cell 14 can comprise an ionically conductive reference cell electrolyte 40. An outer reference electrode 42 is disposed on one side of the reference cell electrolyte 40 while an inner reference electrode 44 is disposed on the opposite side of the reference cell electrolyte 40. The inner reference electrode 44 may be in communication with a gas channel 45, which, during operation, can be exposed to reference gas such as air, oxygen, or the like.

Optionally, a second diffusion limiting material (not shown) may be disposed between the inner reference electrode 44 and an insulating layer 50. During operation, it is preferred that the second diffusion limiting material (not shown), if present, be exposed to the reference gas. The second diffusion limiting material can provide fluid communication between the reference gas and the inner reference electrode 44. The second diffusion limiting material may be fabricated from any material, and has a sufficient porosity to permit the flow of reference gas to contact the inner reference electrode 44.

Conductive leads 46 and 48 are in electrical communication with the outer reference electrode 42 and the inner reference electrode 44, respectively. The cell isolation layer 27 and the cell separation layer 28 further include chamber 35 and 36, respectfully, which is coaxial and in fluid communication with the diffusion limiting material 38 and inner pump electrode 24 and outer reference electrode 42. Furthermore, the cell separation layer 28 may optionally not be employed if the voltage drop through the electrolyte is not a factor, such as when the pumping current is small.

As previously discussed, the sensor 10 may further include other components, such as the temperature sensor 16, and the heater 18 shown in FIG. 1. The sensor 10 may also comprise a series of insulating layers 71, 72, for example, disposed between the insulating layer 50 and the temperature sensor 16. The temperature sensor 16 comprises resistor circuitry 70 disposed between insulating layers 72 and an insulating layer 74 with conductive leads 76, 78 extending therefrom. The heater 18 comprises heater circuitry 80 disposed between insulating layer 74 (common to the temperature sensor 16) and insulating layer 82 with conductive leads 84, 86 extending therefrom. Heater 18 can be any heater capable of maintaining the electrode end of the sensor 10 at a sufficient temperature to facilitate the various electrochemical reactions therein.

Vias 54 and 56 are disposed at the peripheral major surfaces of the sensor 10 (insulating layers 26, 82), at the end opposite the electrodes 22, 24, 42, 44, and circuitry 70, 80. Other vias (not shown) are disposed in the various layers for providing electrical communication to the various conductive leads. Contacts 58 and 60 are electrically connected to the leads 30, 32, 46, 48, 76, 78, 84 and 86 through vias 54 and 56, respectively.

The insulating layers 26, 27, 28, 50, 71, 72, 74 and 82 can comprise any insulating material, such as a metal oxide, e.g., aluminum oxide, zirconium oxide, or a similar material, that is capable of inhibiting electrical communication and providing physical protection. Preferably, the insulating layers comprise a material having substantially similar coefficients of thermal expansion, shrinkage characteristics, and chemical compatibility in order to minimize, if not eliminate, delamination and other processing problems. In a preferred embodiment, each insulating layer is fabricated from high purity aluminum oxide, (e.g., greater than or equal to about 96 weight percent (wt %) aluminum oxide) and preferably flux material. The insulating layers may preferably comprise greater than or equal to about 80 wt % aluminum oxide and less than or equal to 20 wt % flux material, with greater than or equal to about 90 wt % aluminum oxide and less than or equal to about 10 wt % flux material more preferred, and greater than or equal to about 96 wt % aluminum oxide and less than or equal to about 4 wt % flux material even more preferred based upon the total weight of the insulating layer composition. The composition of the flux material can be one or more oxides such as silica, lanthanum oxide, aluminum oxide, boron oxide, yttria, and the like, as well as combinations comprising at least one of the foregoing flux materials. An exemplary flux material composition comprises about 47.5 wt % silica, about 22.5 wt % lanthanum oxide, about 22.5 wt % aluminum oxide, about 5 wt % boron oxide and about 2 wt % yttria, based upon the total weight of the flux material.

The pump cell electrolyte 20 and the reference cell electrolyte 40 can be formed of any material that is capable of permitting the electrochemical transfer of oxygen ions while inhibiting the physical passage of exhaust gases, has an ionic/total conductivity ratio of approximately unity, and is compatible with the environment in which sensor will be utilized (e.g., up to about 1,000° C.). Possible solid electrolyte materials can comprise any material conventionally employed as sensor electrolytes, including, but not limited to, metal oxides such as zirconia, and the like, which may optionally be stabilized with calcium, barium, yttrium, magnesium, aluminum, lanthanum, cesium, gadolinium, and the like, and oxides thereof, as well as combinations comprising at least one of the foregoing electrolyte materials. For example, the electrolyte can be aluminum oxide and yttrium stabilized zirconia. Typically, the electrolyte has a thickness of up to about 500 microns, with a thickness of approximately 25 microns to about 500 microns preferred, and a thickness of about 50 microns to about 200 microns especially preferred.

The electrodes 22, 24, 42, 44 can comprise any metal capable of ionizing oxygen, including, but not limited to, metals such as platinum, palladium, gold, osmium, rhodium, iridium, ruthenium, zirconium, yttrium, cerium, calcium, aluminum, and the like, as well as alloys, oxides, and combinations comprising at least one of the foregoing. The electrodes preferably have a porosity sufficient to permit the diffusion of oxygen molecules without substantially restricting such gas diffusion. Typically, the porosity is greater than the porosity of the diffusion limiting material 38.

Furthermore, in order to enhance the fuel gases reacting with the inner pump electrode 24, the inner pump electrode 24 may comprise an additional catalytic material. This additional catalytic material may include rhodium, magnesium, tantalum, lanthanum, strontium, nickel, copper, aluminum, iron, and the like, as well as oxides, alloys, and combinations comprising at least one of the foregoing catalytic materials. Among these, rhodium, copper, aluminum, lanthanum, strontium, iron, and oxides, alloys, and combinations comprising at least one of the foregoing are preferred. Especially preferred are rhodium, copper oxide/aluminum oxide, or lanthana/strontia/iron oxide. The inner pump electrode 24 having this additional catalytic material may be formed by techniques known in the art, such as, for example, by coating the catalyst on the inner pump electrode 24, or by mixing the catalyst in with the electrode ink used to form the inner pump electrode 24.

With respect to the size and geometry of electrodes 22, 24, 42, 44, they are generally adequate to provide current output sufficient to enable reasonable signal resolution over a wide range of oxygen levels while preventing leakage between electrolyte 20, 40. Generally, a thickness of about 1.0 micron to about 25 microns can be employed, with a thickness of about 5 microns to about 20 microns preferred, and about 10 microns to about 18 microns more preferred. The geometry of the electrodes is preferably substantially similar to the geometry of the chamber 36, with at least a slightly larger overall size than the chamber 36 preferred to ensure that the electrodes cover the electrolyte thereby maximizing the pumping efficiency. In one embodiment, the nominal electrode area can be about 6 square millimeters ($mm^2$) to about 7 $mm^2$.

The porous protection layer 34 disposed over pump cell electrode 22 can comprise a spinel (e.g., magnesium aluminum oxide), aluminum oxide, zirconia, and the like, as well as combinations comprising at least one of the foregoing materials. This porous protection layer 34 preferably comprises a sufficient porosity to permit fluid communication between sensing electrode 22 and the sensing atmosphere as well as provide protection from impurities that can cause poisoning or degradation in electrode sensitivity.

The diffusion limiting material 38 preferably comprises porosity-controlled ceramics, such that the oxygen molecular diffusion from the chamber to the outside environment can be regulated by a lower limiting current at a sensor operating temperature of less than or equal to about 500° C. In one embodiment, the diffusion limiting material 38 comprises a first aluminum oxide powder, preferably high purity aluminum oxide (e.g., comprising greater than or equal to 99% aluminum oxide, based upon the total weight of the aluminum oxide), having an average particle size distribution of about 4.5 micrometers to about 5.5 micrometers, and a second aluminum oxide powder, also preferably high purity aluminum oxide powder, having an average particle size of about 0.3 micrometers to about 0.7 micrometers, wherein the particle size is based upon the major diameter of the particle and the particle distributions are Gaussian distributions. The amounts of the aluminum oxide powders can preferably be about 45 wt % to about 55 wt % of each of the first and second aluminum oxide powders, based upon the total weight of the aluminum oxide. Preferably, the particle size distributions are Gaussian distributions centered at about 5 micrometers and about 0.5 micrometers, respectively. Additionally, the diffusion limiting material preferably has a gas permeability such that the limiting current of oxygen in air is about 0.05 milliamperes per square centimeter of pump electrode area ($mA/cm^2$) to about 5 $mA/cm^2$. With respect to the other sensor components, e.g., electrodes 22, 24, 42, 44, electrolytes 20, 40 insulating layers 26, 27, 28, 50, 71, 72, 74, 74, 82, temperature resistor circuitry 70, heater circuitry 80, leads 30, 32, 46, 48, 76, 78, 84, 86, vias 54, 56, 36, contacts 58, 60, diffusion limiting materials 38, 52, and the like, are formed using techniques such as screen printing, tape casting methods, sputtering, punching and place, spraying (e.g., electrostatically spraying, slurry spraying, plasma spraying, and the like), dipping, painting, and the like, as well as combinations comprising at least one of the foregoing techniques, as is appropriate. For example, electrode 22 can be screen printed onto the pump cell electrolyte 20. Conductive leads 30, 32, 46, 48, 76, 78, 84 and 86 and any vias, e.g., 36, 56, 54, are typically formed simultaneously. The components are then laid-up in accordance with the particular type of sensor. The sensor is then heat treated to laminate the layers together. Typically, the sensor is heated to a temperature of about 1,400° C. to about 1,550° C. for a sufficient period of time to fully fire the layers, with a temperature of about 1,450° C. to about 1,510° C. preferred, for a period of up to about 3 hours or so, with about 100 minutes to about 140 minutes preferred.

The operation of the sensor is explained with reference to FIG. 2, which depicts a cross-sectional view of the sensor, and which is generally labeled as sensor 100. Gases comprising, for example, oxygen, hydrogen, hydrocarbons, sulfur, and the like, and mixtures thereof, collect in a chamber 101 by means of a diffusion pathway formed by a diffusion limiting material 102, which is disposed between ionic isolation layers 109. Gases may also enter the sensor by means of a gas vent 103, which is in physical communication with an inner reference electrode 104. A voltage is applied across a pump cell 106 to generate a current between the inner pump electrode 107 and the outer pump electrode 108. When the oxygen concentration in the chamber 101 reaches a predetermined value, such as zero, the sensor's 100 limiting current has been reached.

The limiting current should be sufficient to indicate a predetermined oxygen concentration located in chamber 101 while allowing the sensor to operate at temperatures below the auto-ignition temperature of the gases to which the sensor is exposed. Limiting currents can be about 0.005 to about 0.20 mA. Within this range, a limiting current of greater than or equal to about 0.008 mA is preferred, with greater than or equal to about 0.01 mA more preferred. Also within this range, a limiting current of less than or equal to about 0.15 mA is preferred, with less than or equal to about 0.10 mA more preferred.

As used herein, the auto-ignition temperature is the minimum temperature required to initiate or cause self-combustion without ignition from an external source of energy. Suitable operating temperatures of the present sensor include temperatures of about 300° C. to about 700° C. Within this range, a temperature of greater than or equal to about 350° C. is preferred, with greater than or equal to about 400° C. more preferred, and greater than or equal to about 450° C. especially preferred. Also within this range, a temperature of less than or equal to about 600° C. is preferred, with less than or equal to about 550° C. more preferred, and less than or equal to about 500° C. especially preferred.

Both the preferred limiting current values and sensor operating temperatures may be achieved by means of the diffusion limiting material. The diffusion limiting material is much denser than typical diffusion limiting material used in a typical sensor. When oxygen diffuses through the diffusion limiting material into the pump chamber, it is pumped through the pump cell. If the amount of oxygen diffusing into the pump chamber is considerably high, the sensor has to operate at high temperature for higher oxygen ion conductivity. Restriction of the diffusion limiting material reduces the rate of the oxygen diffusing through the diffusion limiting material. Therefore, this diffusion limiting material allows oxygen ion conductivity at a lower operating temperature in electrolyte. If the limiting current of air (without reducing gases) is higher than 5 mA per nominal electrode area of 1 cm² (mA/cm²), the pump electrode will require a polarization voltage high enough to create an electrolysis effect on $H_2O$, $CO$, $CO_2$, or even the zirconia itself. If the limiting current of air is lower than 0.05 mA/cm2, the current level will be too low to be detected without noise problem.

Figure 2:
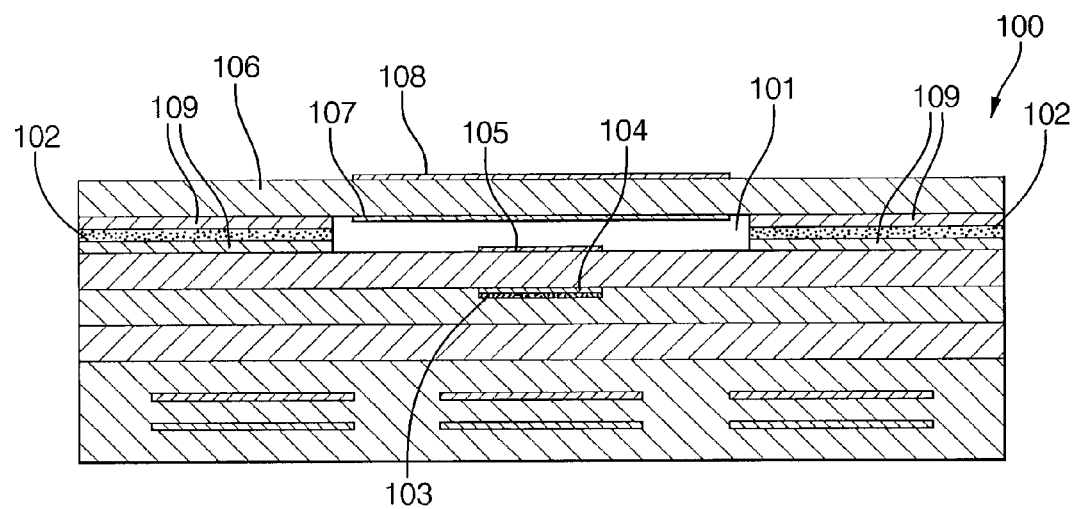
FIG. 2 is a schematic representation of a cross-sectional view of the sensor.

Referring still to FIG. 2, when the limiting current passes through a resistor (not shown), a voltage output is obtained. This voltage is the output of the sensor 100. Because the oxygen is capable of reacting with the reducing gases (e.g., hydrocarbons (such as methane and the like), hydrogen, carbon monoxide, and the like), for example, located in the chamber 101, the voltage output of the sensor is indicative of the levels of oxygen and reducing gases to which the sensor 100 is being exposed. That is, the greater the concentration of reducing gases within the chamber 101, the more oxygen will be consumed in the chemical reactions with these reducing gases, and hence, the lower will be the voltage output of the sensor 100. Therefore, the oxygen content available to be pumped out through the pump cell 106 is reduced in proportion to the amount of the reducing gases diffusing through the diffusion limiting material 102.

Figure 3:
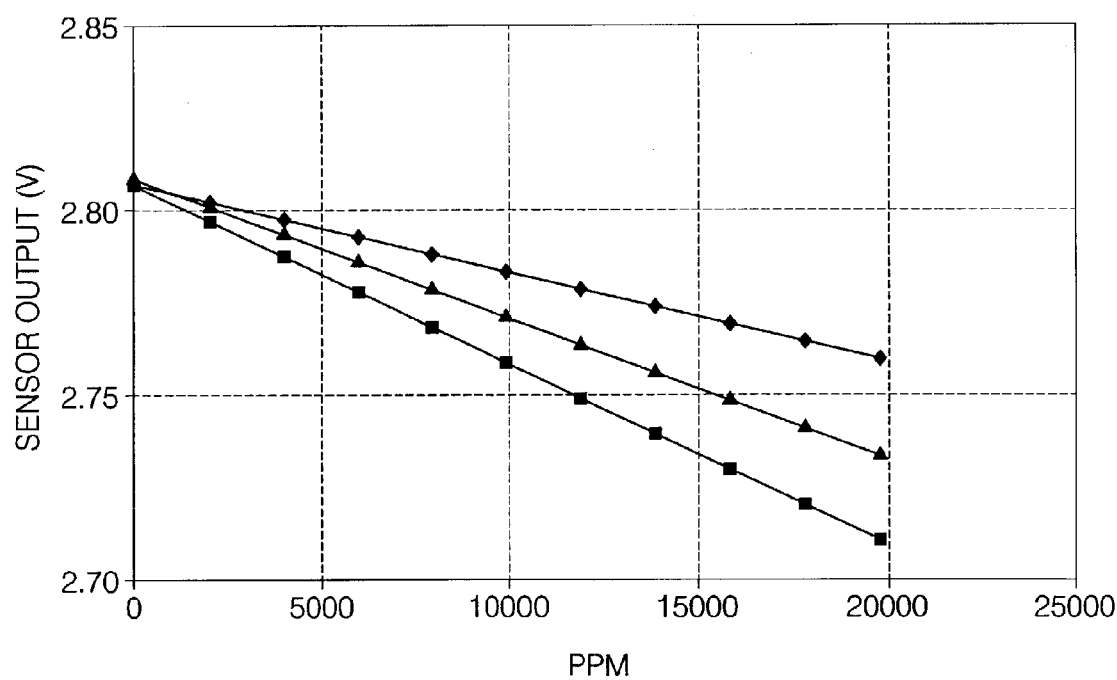
FIG. 3 is a graph depicting sensor output as a function of reducing gas concentration.

Thus, the output voltage decreases linearly in accordance with the unique slope associated with each reducing gas. When there are multiple reducing species, such as hydrogen and methane, the voltage output is linearly the summation effect of each individual reducing gas. Therefore, as shown in FIG. 3, as the concentration of hydrogen (shown by diagonals) increases from 0 to about 20,000 parts per million (ppm), the voltage output, which is indicative of the amount of oxygen contained in the chamber, gradually decreases in a linearly, proportional manner. The same is true for the effect of increasing amounts of methane (shown by squares). Increasing the concentration of a combination of hydrogen and methane (shown by triangles) also has a proportionately linear lowering effect on the oxygen concentration, wherein the effect is a summation of the results found with the individual hydrogen and methane samples. Once the limiting current has been reached, an emf signal formed between an inner reference electrode 104 and an outer reference electrode 105 is used by the sensor 100 to control the pump cell 106 such that the sensor 100 can continue operating at current limiting mode.

The sensor may further comprise an electronics system wherein the temperature of the sensor may be controlled. The electronics system may use a sine wave signal to monitor the electrolyte impedance between the two reference electrodes. Additionally, the electronics system may use the electrolyte impedance data for a feed back temperature control of the sensor. The electronics system can also include a low pass filter to allow for the separation of the electromotive force (emf) signal, as generated by the reference electrodes, and the temperature controlling sine wave, and to use the emf signal to control the pump cell operated at current limiting mode.

Figure 4:
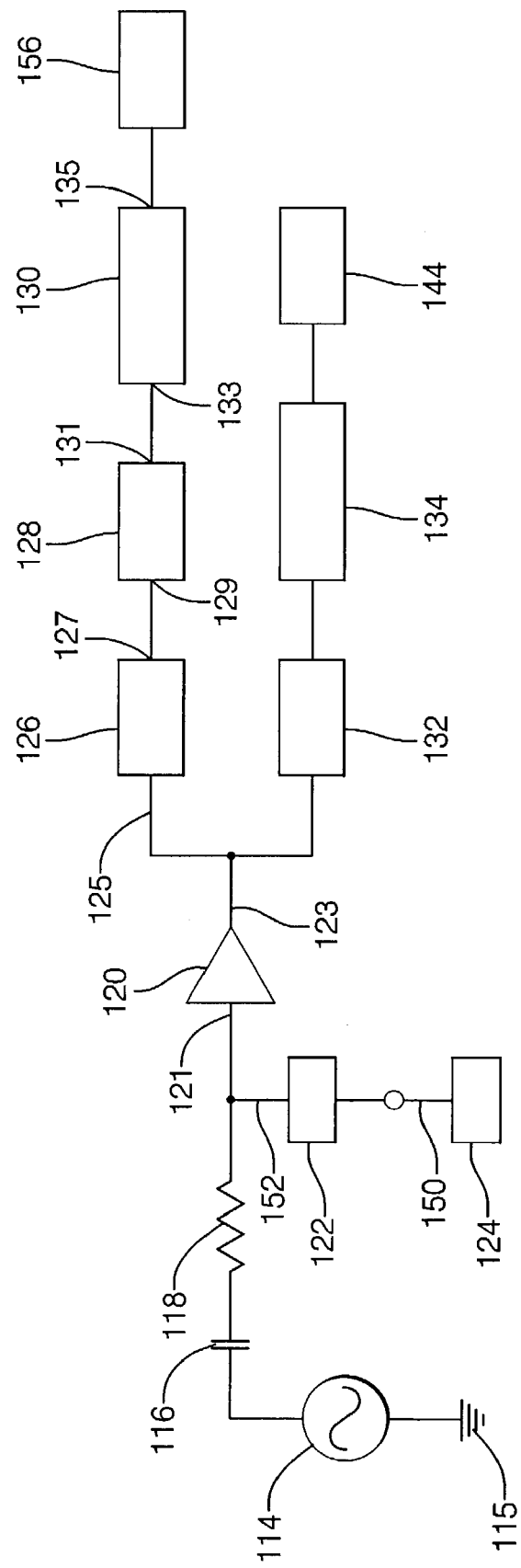
FIG. 4 is a block diagram of a system for controlling the temperature of an oxygen sensor.

FIG. 4 depicts a system for controlling the temperature of sensor 122. The system includes a signal capacitor 116, a voltage divider resistor 118, a signal buffering circuit 120 having a buffer input 121 and a buffer output 123, a high pass filter 126 having a filter input 125 and a filter output 127, an alternating current (AC) amplitude to direct current (DC) converter 128 having a detect input 129 and a detect output 131 and a signal amplifier 130 having an amplifier input 133 and an amplifier output 135. In accordance with an embodiment of the disclosure, signal generator 114 is preferably communicated with a ground potential 115 and with voltage divider resistor 118 through signal capacitor 116. Voltage divider resistor 118 is also preferably communicated with buffer input 121 and a reference cell 14, as described in FIG. 1 above via positive lead 152. Buffer output 123 is in turn communicated with filter input 125 and filter output 127 is preferably communicated with detect input 129. Detect output 131 is preferably communicated with amplifier input 133 and amplifier output 135 is communicated with heating control device 156.

A fixed frequency sinusoidal signal is then introduced to the reference cell 14 so as to create a response signal responsive to the temperature of the reference cell 14. In accordance with an embodiment of the present disclosure, the sinusoidal signal is preferably a fixed frequency sinusoidal signal having a peak-to-peak voltage potential of about 0.2 volt to about 0.8 volt. The sinusoidal signal is preferably serially introduced to the reference cell 14 via positive lead 152 in a continuous fashion using signal generator 114 through signal capacitor 116 and voltage divider resistor 118. Also, in accordance with an embodiment of the present disclosure, signal generator 114, signal buffering circuit 120, high pass filter 126, AC amplitude to DC converter 128 and signal amplifier 130 are powered by a constant reference voltage potential 124. In addition, a constant reference voltage potential 124 equal to one half of the constant reference voltage potential which is used to power the whole signal conditioning circuit, as described hereinabove, is applied to negative lead 150.

As the sinusoidal signal is applied to the reference cell 14, the introduced sinusoidal signal is added to the reference cell 14, so as to be superimposed on top of the normal function of the reference cell 14. The AC magnitude of the applied sinusoidal signal at positive lead 152 will respond in an inversely proportional manner to the temperature of the reference cell 14. As the temperature of the reference cell 14 increases, the impedance of the reference cell 14 decreases causing the AC voltage potential magnitude at the positive lead 152 to decrease. This is because, at any given frequency, the complex impedance of the solid electrolyte construction of the reference cell 14 can be represented in polar coordinates as:

$$Z^* = Z_0(T,f)\exp[i\theta(T,f)],$$

where: T is the temperature of reference cell 14, and
f is the applied sinusoidal signal frequency $$Z_0 = \{[R_0(1+A^2)+R]^2 + A^2 R^2\}^{1/2}/(1+A^2);$$

$$\theta = \tan^{-1}\{AR/[R_0(1+A^2)+R]\}; \text{ and}$$

$$A = 2\pi f C R,$$

where: C is the grain boundary capacitance that is constant with temperature,
$R_0$ is the grain, and
R is the grain boundary resistance, In addition, $R_0$ and R are Arrhenius equations having activation energy's close to each other. Because of this, $Z_0(T,f)$ is a monotonic function of the temperature of the reference cell 14 at any fixed frequency f.

In accordance with an embodiment of the sensor, the fixed frequency sinusoidal signal may be of any frequency suitable to the desired end purpose. Referring to the polar equation hereinabove, the frequency of the sinusoidal signal is preferably chosen such that the complex phase angle θ is lowest at the highest temperature value of a desired temperature range. It should be recognized that two constraints exist regarding the selection of the frequency of the sinusoidal signal. The first constraint is that if the frequency of the signal is too high, the control sensitivity of the response signal will be impeded. The second constraint is that if the frequency is too low, the impedance of the inner reference electrode 44, as shown in FIG. 1, and the impedance of the outer reference electrode 42, as shown in FIG. 1 will be included with the reference cell impedance. This is undesirable because the electrode impedances are a function of the ambient gas composition and will influence the control of the sensor temperature.

The response signal, seen at positive lead 152, is then buffered using a signal buffering circuit 120 so as to create a buffered signal. By applying the response signal to the buffer input 121, a conditioned, or buffered signal is created wherein the buffered signal is isolated from the response signal. In accordance with an embodiment of the present disclosure, the buffered signal includes a high frequency signal component and a low frequency signal component wherein the high frequency signal component is responsive to the temperature of reference cell 14 and the low frequency signal component is used as the feedback control signal to oxygen pump 144.

The buffered signal is then applied to high pass filter 126, so as to filter out the low frequency signal component and create a filtered signal having a filtered signal magnitude. This filtered signal is the isolated AC portion of the buffered signal and the filtered signal magnitude is responsive to the reference cell temperature. In accordance with an embodiment of the present disclosure, the filtered signal magnitude is inversely proportional to the temperature of reference cell 14.

The filtered signal is then applied to detect input 129 of AC amplitude to DC converter 128 so as to convert the AC signal into a DC signal and create a temperature signal at detect output 131 responsive to the magnitude of the filtered signal. The temperature signal at detect output 131 is then applied to a signal amplifier 130 so as to cause the temperature signal to be amplified. The amplified temperature signal at amplifier output 135 is then communicated to the heating control device 156 so as to cause the heater 18, as shown in FIG. 1, to respond to the temperature signal.

In addition, the buffered signal is applied to a low pass filter 132, so as to filter out the high frequency signal component. The output from low pass filter 132 is then applied to a DC amplifier 134 so as to create a feedback control signal used to control oxygen pump 144.

The sensor disclosed herein has several advantages over other sensors. Compared to typical air-reducing gas sensors (e.g., metal oxide conducting sensors, metal-gate-field-effect silicon sensors, or calorimetric catalyst types of sensors), the present sensor has a fast response time (less than or equal to about 0.1 sec, since no metal or metal oxide bulk diffusion mechanisms are involved), and no delayed recover time (since there is no gas desorption effect of the metal-gate, metal oxide, or thermal-mass delay (effect caused by the calorimetric thermal reaction energy redistribution)) after exposure to reducing gases. In addition, the disclosed sensor is more robust to contamination (as protection coating layers are put on top of the electrodes) and has no signal drifting problem (the signal level is controlled by the gas-diffusion-limiting means which is not changed with time, as is the catalysts in the calorimetric sensors and the metal-gate of silicon field effect sensors).

Compared to typical wide range air to fuel ratio zirconia pump sensor without the present disclosed diffusion limiting material, the advantage is the lower operating temperatures under which the sensor can function. Lower operating temperatures increases the overall durability of the sensor as it reduces the functional decline of the heat-sensitive sensor components (thermal aging effect). In addition, operating the sensor at temperature lower than the auto-ignition temperature allows its usage as a reducing gas leakage detector.

It should be noted that the present disclosure encompasses a sensor wherein the reference electrode may be connected either to the ambient air, or alternatively, to the same air to which the outer pump electrode is exposed by means of an air channel. When the sensor comprises a reference electrode connected in the latter, an economic sensor package can be applied here, since there is no need to design an expensive air pocket which is isolated from the ambient air.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A sensor comprising:
   a pump cell comprising:
      an inner pump electrode;
      an outer pump electrode;
      a pump cell electrolyte layer interposed between the inner pump electrode and the outer pump electrode; and
      a cell isolation layer disposed on the inner pump electrode on a side opposite the pump cell electrolyte,
   a reference cell in operable communication with the pump cell, the reference cell comprising an outer reference electrode and an inner reference electrode, and a reference cell electrolyte interposed between the outer reference electrode and the inner reference electrode; and
   a diffusion limiting material flanking both sides of a chamber formed between the cell isolation layer and a cell separation layer, wherein the cell separation layer comprises a via coaxial and in fluid communication with the inner pump electrode, the diffusing limiting material, and the outer reference electrode, and wherein the diffusion limiting material has a gas permeability such that the limiting current of oxygen in air is about 0.05 mA to about 5 mA per cm² of pump electrode area said diffusion limiting material comprising aluminum oxide wherein 45 wt % to about 55 wt % of said aluminum oxide has a first particle size distribution of about 4.5 micrometers to about 5.5 micrometers and the balance has a second particle size distribution of about 0.3 micrometers to about 0.7 micrometers.

2. The sensor of claim 1, further comprising a porous protection layer in fluid communication with the outer pump electrode.

3. The sensor of claim 1, wherein the inner pump electrode, the outer pump electrode, the inner reference electrode, and the outer reference electrode individually includes a first material comprising platinum, palladium, gold, osmium, rhodium, iridium, ruthenium, zirconium, yttrium, cerium, calcium, aluminum, alloys of the foregoing, oxides of the foregoing, or combinations comprising at least one of the foregoing first materials.

4. The sensor of claim 3, wherein the inner pump electrode comprises an additional material comprising platinum, palladium, rhodium, iridium, osmium, magnesium, ruthenium, tantalum, lanthanum, strontium, zirconium, yttrium, cerium, nickel, copper, aluminum, iron, alloys of the foregoing, oxides of the foregoing, or comprising at least one of the foregoing additional materials.

5. The sensor of claim 4, wherein the inner pump electrode comprises rhodium, copper oxide/aluminum oxide, or lanthana/strontia/iron oxide.

6. The sensor of claim 1, further comprising a heater for maintaining the reference cell and sail pump cell at a temperature sufficient to facilitate an electrochemical reaction.

7. The sensor of claim 1, further comprising means for analysing a limiting current produced by the pump cell.

8. The sensor of claim 7, wherein the limiting current comprises about 0.005 to about 0.20 milliamps.

9. A method for measuring concentration of a reducing constituent selected form the group consisting of hydrocarbon, hydrogen, and carbon monoxide in a gas comprising:
exposing a sensor to air, wherein the sensor comprises a pump cell, a reference cell, and a cell separation layer interposed between the pump cell and the reference cell, wherein the pump cell comprises an outer pump electrode exposed to the gas, an inner pump electrode in operable communication with a diffusion limiting material by means of a cell isolation layer, and a pump cell electrolyte interposed between the inner pump electrode and the outer pump electrode, wherein the reference cell comprises an outer reference electrode in operable communication with the diffusion limiting material, an inner reference electrode in fluid communication with a reference gas source and a reference electrolyte interposed between the outer reference electrode and the inner reference electrode, and wherein the diffusion limiting material comprises a gas permeability such that the limiting current of oxygen in air is about 0.05 mA to about 5 mA per cm² of pump electrode area applying a voltage to the outer pump electrode and the inner pump electrode to form a limiting current;

diffusing oxygen molecules and reducing gases across the diffusion limiting material;

generating an electromotive force signal between the outer reference electrode and the inner reference electrode;

adjusting the pump current to maintain the electromotive force signal at a predetermined value, wherein the limiting current is proportional to the reducing gases.

10. The method of claim 9, wherein the sensor operates at a temperature of about 300° C. to about 700° C.

11. The method of claim 10, wherein the sensor operates a temperature less than or equal to 500° C.

12. The method of claim 9, wherein the limiting current comprises about 0.005 to about 0.20 milliamps.

13. The method of claim 9, wherein the limiting current is less than or equal to about 0.10 milliamps.

14. The method of claim 9, wherein the diffusion limiting material comprises aluminum oxide having a first particle size distribution of about 4.5 micrometers to about 5.5 micrometers and a second particle size distribution of about 0.3 micrometers to about 0.7 micrometers.

15. The sensor of claim 14, wherein the aluminium oxide comprises 45 wt % to about 55 wt % of each of the aluminum oxide having the first particle size and the aluminum oxide having the second particle size, based upon the total weight of the aluminum oxide.

* * * * *